United States Patent [19]
Ogawa et al.

[11] Patent Number: 5,370,714
[45] Date of Patent: Dec. 6, 1994

[54] METHOD OF CULTIVATING MUSHROOMS AND WOODY CULTURE MEDIUM THEREFOR

[75] Inventors: Makoto Ogawa, Hirakata; Takeshi Itoh, Ayabe; Noriaki Seki, Tokyo, all of Japan

[73] Assignee: Kansai Environmental Engineering Center Co., Ltd., Osaka, Japan

[21] Appl. No.: 93,873

[22] Filed: Jul. 20, 1993

[30] Foreign Application Priority Data

Jul. 21, 1992 [JP] Japan .................... 4-193840

[51] Int. Cl.$^5$ ............................ A01G 1/04
[52] U.S. Cl. ............................ 47/1.1; 71/5
[58] Field of Search ............. 47/1.102, 1.104, 1.107, 47/1.1

[56] References Cited

U.S. PATENT DOCUMENTS 5,169,968 12/1992 Rice .................... 554/193

FOREIGN PATENT DOCUMENTS 53-12155 9/1978 Japan .
53-107476 9/1978 Japan .
1242050 7/1986 U.S.S.R. .

*Primary Examiner*—David T. Fox
*Assistant Examiner*—Erich E. Veitenheimer
*Attorney, Agent, or Firm*—Wenderoth, Lind & Ponack

[57] ABSTRACT

There is provided a culture medium for cultivating mushrooms whose material can be selected from a variety of woody materials and which can be transported in a compact form. There is also provided a method of cultivating mushrooms using such a culture medium in which pathogenic and other germs are less likely to breed and with which mushrooms can be cultivated in shorter periods. After adding nutrients such as rice and wheat brans, a mixture of dried sawdust and chip dust is heated at 150°–500° C. for 1–5 minutes under a pressure of 1.0–3.0 t/cm$^2$ to form a cylindrical woody culture medium. The medium thus obtained is allowed to swell by adding water and then sterilized by sealing it in a bag. Mushroom fungi is then inoculated into it.

1 Claim, No Drawings

METHOD OF CULTIVATING MUSHROOMS AND WOODY CULTURE MEDIUM THEREFOR

FIELD OF THE INVENTION

This invention relates to a method of cultivating mushrooms and a woody culture medium therefor.

In general, the term "mushroom" does not refer to a taxonomical unit but to basidiomycetes and ascomycetes forming large fruit bodies or to fruit bodies themselves.

BACKGROUND OF THE INVENTION

In order to grow such edible mushrooms as *Flammulina velutipes, Pleurotus ostreatus, Hypsizigus marmoreus, Pholiota nameko,* and *Grifola frondosa,* it is known to use a culture medium containing such nutrients as sawdust, rice bran and wheat bran. Before inoculating a mushroom spawn to the culture medium, it is put in a plastic bag or a glass container, sterilized for one hour at 120° C. under the pressure of 1.2 atm. in a high-pressure sterilizing oven (autoclave), and then cooled. Now, this technique is also employed in growing *Lentinus edodes.*

This method is superior to the conventional one in which mushroom spawns are inoculated on logs, because it saves a lot of labor and permits a planned mass-production of mushrooms. Thus, this technique is now widespread.

But in this method in which sawdust or the like is used as a culture medium, it takes a long time to sufficiently mature sawdust for use as nutrients for fungi. Thus the productivity is low and the cost too high.

Further, wood of conifers from which sawdust is produced, contain some growth inhibitors for mycelium such as terpene compared to broad-leaved trees. Further, the speed at which such sawdust is decomposed and the mycelium is matured is rather slow. Its use is thus difficult. Actually, sawdust of conifers such as *Cryptomeria japonica* is used together with an excessive amount of nutrients as a substitute for broad-leaved trees. But because such a culture medium contains an excessive amount of nutrients, pathogenic germs such as Trichoderma and other various germs such as green mold tend to grow.

SUMMARY OF THE INVENTION

An object of this invention is to provide a method of cultivating mushrooms in which various kinds of materials including both coniferous and broad-leaved trees can be used as the woody materials for a culture medium and which makes it possible to reduce the size of such culture medium for easy transportation, to prevent the growth of pathogenic and other germs, and to cultivate mushrooms in short periods.

DESCRIPTION OF THE PREFERRED EMBODIMENTS

According to this invention, there is provided a method of cultivating mushrooms comprising the steps of forming a culture medium comprising as main components water and woody materials heated at 150°–300° C. for 1–5 minutes under the pressure of 1.0–3.0 t/cm$^2$ and inoculating the culture medium with a spawn.

As a culture medium, woody materials heated at 150°–300° C. for 1–5 minutes under the pressure of 1.0–3.0 t/cm$^2$ are used.

With the method according to this invention, woody materials such as sawdust and chips as the main components of the culture medium are subjected to preliminary treatment in which they are heated at a relatively high temperature of 150°–300° C. for a relatively short period of 1–5 minutes. This treatment serves to reduce the amounts of substances that may inhibit the growth of mycelium, such as resin and oils, terpene, phenolic compounds and other volatile components. This makes it possible to use plant materials other than broad-leaved trees as the culture medium.

When the material that has been denatured by being heated at such a high temperature is treated at a high pressure of 1.0–3.0 t/cm$^2$, it softens to such an extent that one can observe under a microscope how its tissue has been broken. As lignin and cellulose are partially destroyed by physical and chemical treatments, the culture medium provides ideal conditions for fungal growth. By being pressured, the volume of the woody material is reduced. Thus, the culture medium according to the present invention can be transported much more easily than conventional sawdust.

According to this invention, both conifers and broad-leaved trees can be used as the woody material for culture medium. Also, such a culture medium makes it possible to reduce the cost for cultivating mushrooms and to increase the speed of growth of mycelium. Moreover, such a culture medium can reduce the number of pathogenic and other germs generated during cultivation and shorten the growing period.

The woody materials used in this invention may be broad-leaved trees such as beech, zelkova or oak trees or conifers such as Japanese cedars (Cryptomeria), Japanese latches (Larix), firs (Akies) or pine (Pinus). Such woody materials may be in the form of sawdust or chips, which are by-products of lumbering, or logs or used medium of mushrooms. Nutrients such as rice bran or wheat bran may be added to such woody material to improve the quality of the culture medium.

The woody material thus prepared is heated at 150°–300° C. for 1–5 minutes under the pressure of 1.0–3.0 t/cm$^2$. If the temperature is less than 150° C., it will be difficult to sufficiently remove the growth inhibitors by evaporation and thus to improve the growth rate of mycelium. If higher than 300° C., which is the ignition point of the raw material, even the beneficial components would suffer thermal denaturation or burn.

If the pressure is less than 1.0 t/cm$^2$, it will be difficult to sufficiently decompose lignin and cellulose. If higher than 3.0 t/cm$^2$, the mycelial growth rate cannot be increased any further. Thus, such a high pressure is unpractical.

Mushrooms to which the cultivation method of the present invention is applicable are not limited to specific species. It is applicable mainly to edible fungi such as *Lentinus edodes, Hypsizigus marmoreus, Flammulina velutipes, Pholiota nameko, Pleurotus ostreatus, Grifola frondosa,* etc. and to medicinal mushrooms.

[EXAMPLE 1]

A mixture of sawdust and chip dust (volume ratio of the former to the latter being 7: 3) of broad-leaved trees, mainly of beech was put in a rotary heat drier and dried at 150° C. for 3–5 minutes. Its volume reduced to half after drying and its color turned slightly darker. 45 kg of nutrient, mainly of rice and wheat bran, (made by Hokken: Baidel)(hereinafter referred to as nutrient A) was added to 225 kg of the dried sawdust.

The mixture thus formed was fed into an extruder (made by Takahashi Seisakusho: wood fuel extruder) and heated for one minute at 300° C. under the pressure of 1.5 t/cm$^2$ (feed rate: 90 cm/min.) to form the mixture into a cylindrical shape. The cylindrical material thus formed was cut into pieces, each piece weighing about 460 g. These pieces were used as woody culture medium.

Each culture medium was put in a polypropylene bag for use in cultivating mushroom and water was added thereto to allow the medium to swell until its water content reaches 62%. The culture medium thus obtained weighed 1.2 kg, which is the same weight as a conventional fungal culture bed of sawdust.

The culture medium obtained was heated to 120° C. at 1.2 atm. in an autoclave for sterilization and then cooled. Then, a *Lentinus edodes* (produced by Hokken Sangyo: Hokken B00)(strain in which small fruit bodies grow rapidly and simultaneously; hereinafter referred to as strain a) was inoculated into the culture medium under sterile conditions and cultivated in a culture room kept at 22° C. in temperature and 55% in humidity.

The mycelial growth (up to 68th day from the beginning of cultivation), the change in weight of each fungal bed and the number and weight of fruit body (yield) per fungal bed from the 60th day till 149th day were measured. The results are shown in Tables 1-3. The treatment for the fructification was started on the 60th day from the beginning of cultivation, because by that time, mycelium was fully matured.

In the first treatment for fructification, the fungal beds were placed in a fruiting room kept at 17° C. in temperature and 85% in humidity under light condition. After confirming fructification in the bag, the fungal bed was taken out of the bag and the humidity was increased to 95% to accelerate the growth. After the first harvesting, the fungal bed was put in a culture room to rest for 20 days. Then on the 90th day, the second treatment was carried out by immersing the fungal bed in water and sprinkling water. Fruit bodies produced were collected one after another.

[EXAMPLE 2]

The nutrient comprising mainly rice bran and wheat bran, that is, Kinogen manufactured by Meiji Seika (hereinafer referred to as nutrient B) was added to the mixture of sawdust and chip dust, and was used as a culture medium. The fungus inoculated was *Lentinus edodes* (manufactured by Meiji Seika: Meiji 904)(strain in which large fruit bodies occur over long term; hereinafter referred to as strain b). It was cultivated till the 59th day under the same growing conditions as in EXAMPLE 1. Thereafter, the growth treatments were carried out in the following manner.

Namely, the fungal bed was taken out of the bag and placed in a fruiting room kept at 24° C. in temperature and 95% in humidity while sprinkling or pouring water. The measurements as described in EXAMPLE 1 were conducted for respective periods. The results are shown in Tables 1-3.

[Comparative Example 1]

45 kg of nutrient A was added to 225 kg of the mixture of sawdust and chip dust used in EXAMPLE 1 (after drying) and its water content was adjusted to 62% by adding water. 1.2 kg each of the mixture thus obtained was put in a polypropylene bag for cultivating mushrooms and sterilized in an autoclave for one hour at 120° C. under the pressure of 1.2 atm. The mixture was then cooled to normal temperatures to provide a culture medium.

Strain a was inoculated into the culture medium under sterilized condition. It was then cultivated in exactly the same way as in EXAMPLE 1 and measurements and observations were made for respective periods. The results are shown in Tables 1-3.

[Comparative Example 2]

Strain b was cultivated till the 59th day using nutrient B in exactly the same way as in Comparative Example 1. Thereafter, the same treatments as in EXAMPLE 2 were carried out until the 59th day. Observations and measurements were made in the same way as in the other examples. The results are shown in Tables 1-3.

We will now analyze the results of measurements and observations in the Examples and Comparative examples as to the following items: "growth of mycelium", "maturation of mycelium", "decomposition of sawdust", "fructification" and "microbial contamination".

(Growth of Mycelium)

As shown in Table 1, the growth of mycelium as observed from outside the culture bag was slow initially in EXAMPLES 1 and 2 and apparently faster in Comparative Examples 1 and 2. But the density of mycelium was higher in the former than in the latter when the insides of several fungal beds were observed on the 30th day after cutting. Also, in the former, the mycelium had matured sufficiently by that time and their amount was greater than the latter. On the 48th day, EXAMPLES 1 and 2 had matured almost completely and the sawdust was decomposed sufficiently.

(Maturation of Mycelium)

In case of *Lentinus edodes*, one can judge the degree of maturity of mycelium by the browning and the formation of bean-size lumps on the surface of the fungal bed. Generally, the browning of mycelium appears in 90-120 days. But in EXAMPLES 1 and 2, the browning of mycelium began on the 50th day and almost ended on the 60th day. On the other hand, in Comparative Examples 1 and 2, mycelium had not matured on the 74th day yet. Browning proceeded slowly.

(Decomposition of sawdust)

On the 60th day from the beginning of cultivation, the respective fungal beds were broken in half to observe the degree of decomposition of sawdust. In EXAMPLES 1 and 2, sawdust was decomposed considerably. The interior of the fungal bed was dark brownish in color and sawdust collapsed into a powdery state by pressing the bed lightly. It was also confirmed under microscope that the cells had been broken. On the other hand, in Comparative Examples 1 and 2, sawdust remained undecomposed. The interior of the fungal bed was still light brownish.

Table 2 shows the rate of reduction in weight of each fungal bed while being cultivated. In EXAMPLES 1 and 2, the rate already began to increase on the 32nd day. By the 68th day, the reduction rate was about twice the rate in Comparative Examples 1 and 2. This high reduction rate clearly reflects the apparent fast decomposition.

(Fructification)

In EXAMPLE 1 and Comparative Example 1 (in both examples, strain a and nutrient A were used), the first fruiting ended by the 89th day. But as shown in Table 3, the number of fruit bodies per fungal bed was 23 in average, the total weight being 235 g. The yield was substantially greater than that of Comparative Example 1. Thus, a large number of fruit bodies were harvested at a time. Also, in EXAMPLE 1, four fruit bodies, 53 g in weight, were harvested per fungal bed during the period between 90th and 149th day. The number of fruit bodies harvested during the whole cultivation period was 27.9 per bed, the weight being 288.1 g. Particularly in the secondary occurrence, the yields were again much greater than those of Comparative Example 1.

On the other hand, in EXAMPLE 2 and Comparative Example 2 (in both examples, strain b and nutrient B were used), the former produced large and high-quality fruit bodies from an early state (the 85th day) of cultivation. By the 149th day, 10.4 fruit bodies, 183.8 g in weight, were harvested on the average per bed. They excelled those obtained in Comparative Example 2 both in quality and quantity.

(Microbial Contamination)

above-described treatments in the process of the invention for production of culture medium.

TABLE 1

| Item Number | Average amount of growth of mycelium with lapse of days (in mm) | |
|---|---|---|
| | 27 days | 33 days |
| Example | | |
| 1 | 0.36 | 0.38 |
| 2 | 0.45 | 0.46 |
| Comparative Example | | |
| 1 | 0.47 | 0.53 |
| 2 | 0.51 | 0.49 |

TABLE 2

| Item Number | Reduction in weight of fungal bed with lapse of days (in %) | | |
|---|---|---|---|
| | 32 days | 52 days | 68 days |
| Example | | | |
| 1 | 2.3 | 4.5 | 6.3 |
| 2 | 2.3 | 5.1 | 8.9 |
| Comparative Example | | | |
| 1 | 1.7 | 3.4 | 4.6 |
| 2 | 1.4 | 2.8 | 4.4 |

TABLE 3

| Item Number | Number and weight of fruit bodies produced with lapse of days | | | | | | | | | |
|---|---|---|---|---|---|---|---|---|---|---|
| | 60–89 days | | 90–109 days | | 110–129 days | | 130–149 days | | Total to 149 days | |
| | (Number) | (Gram) | (Number) | (Gram) | (Number) | (Gram) | (Number) | (Gram) | (Number) | (Gram) |
| Example | | | | | | | | | | |
| 1 | 23.9 | 235.0 | 0 | 0 | 0.8 | 16.3 | 3.2 | 36.8 | 27.9 | 288.1 |
| 2 | 0 | 0 | 8.7 | 133.7 | 1.2 | 21.6 | 0.5 | 18.1 | 10.4 | 183.8 |
| Comparative Example | | | | | | | | | | |
| 1 | 10.5 | 126.7 | 1.0 | 35.2 | 0.3 | 6.2 | 0.6 | 4.5 | 12.4 | 172.6 |
| 2 | 0 | 0 | 0 | 0 | 1.0 | 52 3 | 1 0 | 37.4 | 2.0 | 89.7 |

In EXAMPLES 1 and 2, contamination by bacteria and fungi was very low in the fungal bed during cultivation. In fact, no germs were observed unless the bag was broken.

Heretofore, it is considered that the microbial contamination of fungal beds is inevitable after the fructification, but in EXAMPLES 1 and 2, all of the 175 fungal beds used in the experiment remained clean throughout the cultivation period from the beginning of fruiting treatment till the completion of harvest. In contrast, in Comparative Examples 1 and 2, green mold was observed on all the fungal beds. Trichoderma was also observed on some of the beds. The difference is thus apparent. It was clear that the resistance of fungal beds against contamination by microbes increased by the

What is claimed is:

1. A method of cultivating mushrooms comprising the steps of
   extruding a woody material selected from the group consisting of sawdust, chip dust and a mixture thereof produced from trees selected from the group consisting of broad-leaved trees, coniferous trees and both said trees, at 150°–300° C. for 1–5 minutes under a pressure of 1.0–3.0 t/cm$^2$,
   adding water to the extruded woody material in an amount to swell said extruded woody material and provide a culture medium in which mushrooms can grow, and
   inoculating said culture medium with spawn of a mushroom.

* * * * *